United States Patent
Nae-Lih et al.

(10) Patent No.: US 6,168,830 B1
(45) Date of Patent: Jan. 2, 2001

(54) PROCESS FOR FABRICATING CRYSTALLINE METAL OXIDE MATERIAL

(75) Inventors: Wu Nae-Lih; Wang S-yen, both of Taipei (TW)

(73) Assignee: National Science Council of Republic of China, Taipei (TW)

(*) Notice: Under 35 U.S.C. 154(b), the term of this patent shall be extended for 0 days.

(21) Appl. No.: 09/363,979

(22) Filed: Jul. 28, 1999

(51) Int. Cl.$^7$ ................................ B05D 5/00; B05D 3/02
(52) U.S. Cl. ............ 427/215; 427/255.18; 427/255.393; 427/397.7
(58) Field of Search .................. 427/255.393, 255.18, 427/387, 397.7, 397.8, 215, 376.2

(56) References Cited

U.S. PATENT DOCUMENTS

| | | | |
|---|---|---|---|
| 5,501,870 | * 3/1996 | Shiraishi et al. | 427/255.4 |
| 5,593,737 | * 1/1997 | Meinzer et al. | 427/512 |
| 6,027,766 | * 2/2000 | Greenberg et al. | 427/255.5 |

* cited by examiner

Primary Examiner—Shrive Beck
Assistant Examiner—Kirsten A. Crockford
(74) Attorney, Agent, or Firm—Bacon & Thomas

(57) ABSTRACT

The invention relates a process for fabricating crystalline metal oxide materials comprising tin oxide, zirconia, or titania in form as powder, monolith gel or film by first forming a metal oxide material containing —OH surface group through a sol-gel process, and then treating them with $[SiR_m]_n X_z H_y$ compound which reacts with the —OH group to form —OSiR$_m$ surface group, and heating the thus-treated oxide material at a high temperature to crystallize them into a crystalline metal oxide material with high crystallinity, small crystal size (<100 Å) and high surface area (>100 m$^2$/g).

12 Claims, 5 Drawing Sheets

↓ Crystallization at high temperature

↓ Dehydration upon heating

↓ Crystallization at high temperature

↓ Crystallization at high temperature

PROCESS FOR FABRICATING CRYSTALLINE METAL OXIDE MATERIAL

BACKGROUND OF THE INVENTION

1. Field of the Invention

The invention relates a process for fabricating crystalline metal oxide materials comprising tin oxide, zirconia, or titania in form as powder, monolith gel or film by first forming a metal oxide material containing —OH surface group through a sol-gel process, and then treating them with $[SiR_m]_nX_zH_y$ compound which reacts with the —OH group to form —$OSiR_m$ surface group, and heating the thus-treated oxide material at a high temperature to crystallize them into a crystalline metal oxide material with high crystallinity, small crystal size (<100 Å) and high surface area (>100 $m^2/g$).

2. Description of the Prior Art

Transitional and non-transistional metal oxides have been widely used in fields of catalyst and air detection. For example, catalysts based on tin dioxide can be used in organic oxidation (U.S. Pat. Nos. 4,701,437 and 3,947,474) and for controlling quality of waste gases discharged from automobile (U.S. Pat. No. 5,051,393). Monolith gel or film based on tin dioxide can be used for detecting gases such as carbon monooxide and alcohol (U.S. Pat. No. 4,592,967). Catalysts based on titanium dioxide can increase the conversion rate for producing dimer and higher polymer from butylene as starting material (U.S. Pat. No. 5,073,658) and can reduce carbon dioxide and water (J. of Molecular Catalysis, 144 (1997) 207). Titanium dioxide has been used for detecting gases such as carbon monooxide (J. Electrochem. Soc., 144 (1997) 1750–1753) or oxygen (U.S. Pat. No. 4,713,646). Catalysts based on zirconium dioxide ($ZrO_2$) can be used for producing hydrocarbons from synthetic gases (U.S. Pat. No. 5,391,362). On the other hand, zirconium dioxide is able to detect $O_2$ (J. Electrochem. Soc. 144 (1997) 4158–4160).

In the above-listed applications, specific surface area (i.e., the surface area per unit weight of oxide), crystal size and crystallinity are critical material microstructural characteristics that can have effect on their performance in the application. In general, catalyst requires high specific surface area (>100 $m^2/g$) to increase the contact area between reactants and catalyst. As for the gas sensing application, increasing crystallinity can decrease electric power consumption, and reducing crystal size will increase sensitivity of detection. In summary, for applications as catalyst and for gas detection, high specific surface area, small crystal size and high crystallinity (i.e., low lattice defect density) are the preferred microstructural features of the oxides.

Sol-gel process has been extensively used for producing oxide materials of different forms, including powder, monolith gel and film. Sol-gel process involves dissolving a metal alkoxide having a general formula of $M(OR')_x$ where M is metal element, R' is an alkyl group, x is an integer of 1~6, or a water soluble metal salt in an aqueous solution, and carrying out hydrolysis and condensation reactions to obtain a sol:

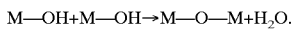

Then, the sol was washed, dried and calcined to yield metal oxide powder or form a monolith xerogel. On the other hand, a thin film can be formed first through coating, and then the film is subject to drying and claciming to yield a metal oxide film. In the course of the sol-gel process, compounds that can form hydrogen ion ($H^+$) or hydroxyl ion ($OH^-$) may be added to change the pH of the solution so as to alter the sol forming rate and the particle dispersion. For example, as described in J. of Non-Crystalline solids 147&148 (1992) 340–345, addition of ammonia water in the aqueous solution of tin tetrachloride can result immediately in a precipitation of sol which was dialyzed or washed repeatedly with fresh water to remove chlorine and ammonium ions. Thereafter, part of water was evaporated by heating to reach a critical concentration, and the residue was then dried to result in an integrally formed monolith xerogel of tin dioxide. Also, as reported in Powder Technology, 92 (1997) 233–239, tetra-isopropyl titanate ($Ti(OCH(CH_3))_4$) was dissolved in iso-propyl alcohol (or n-hexane) and then the solution thus-formed was added with ammonia water (25%) under stirring at 400 rpm. A sol suspension was yielded. After standing for three days, it was filtered and air dried overnight followed by drying at 60° C. one day. The sample obtained was thereafter subjected to heat treatment at 400° C. to yield a titanium dioxide powder. Further, as described in J. Am. Ceram. Soc. 78(1995) 1329–1334, a method for preparing zirconium dioxide powder by sol-gel process comprised of mixing zirconium n-propoxide, 2-propanol, and deionized water in a predetermined ratio at 50° C. for one hour to form an opaque sol precipitate. The precipitate was dried at 120° C. for 24 hours and then washed with fresh water followed by drying to obtain a powder.

Material prepared through sol-gel process, including powder, xerogel or thin film, has, in general, a feature of high specific surface area (>100 $m^2/g$), but has poor mechanical strength and crystallinity. Such material comprises amorphous substances having a large amount of hydroxyl group (—OH). Under heating, such amorphous substance will begin to dehydrate and crystallize wherein its microstructure will change with time, and hence various physical and chemical characteristics thereof varies correspondingly. Therefore, material prepared through sol-gel process should be subjected to a heat treatment to form a crystalline material such that its thermal stability in a practical application can be assured. For example, Goodman et al. in J. Chem. Soc. 237, 1162–67, 1960, stated the preparation of tin dioxide powder by a sol-gel process, wherein, sample just prepared had a specific surface area of 172 $m^2/g$ which, after subjecting to a heat treatment at 500° C., was lowered to 25 $m^2/g$. Nae-Lih Wu et al in J. Am Ceram. Soc.82,67–73 (1999) pointed out that tin dioxide powder prepared by using $SnCl_4$ as the starting material via a sol-gel process contained more than 50% of an amorphous substance whose average crystal size was less than 20 Å, but, after heating at 500° C. for one hour, increased to become 240 Å. Mercera et al. mentioned in Applied Catalysis 57, 127–48 that zirconium dioxide, when used as catalyst support, required a high specific surface area and heat stability. They prepared zirconium dioxide powder by a sol-gel process to obtain an initial specific surface area of 289 $m^2/g$. After heating at 450° C. for 15 hours, due to the growth of crystal, the specific surface area was lowered to be 111 $m^2/g$.

In view of the above-mentioned prior art techniques, it can be clearly seen that the most directly negative effect of the heat treatment process is to cause the overgrowth of crystal and to decrease drastimaticaly the specific surface area. Accordingly, there is a need for a process for fabricating crystalline metal oxide materials, which can lower effectively the negative effect on crystal growth and loss of specific surface area associated with the prior art described above. Specifically, there is a need for a new process to fabricate crystalline metal oxide materials through a sol-gel process which can increase the crystallinity of the material obtained while maintaining the features of small crystal and high specific surface area thereof.

SUMMARY OF THE INVENTION

Accordingly, the object of the invention is to provide a process for fabricating crystalline metal oxide materials comprising tin oxide, zirconia, or titania in form as powder, monolith gel or film by first forming a metal oxide material containing —OH surface group through a sol-gel process, and then treating them with $[SiR_m]_nX_zH_y$ compound which reacts with the —OH group to form —$OSiR_m$ surface group, and heating the thus-treated oxide material at a high temperature to crystallize them into a crystalline metal oxide material with high crystallinity, small crystal size (<100 Å) and high surface area (>100 m²/g).

BRIEF DESCRIPTION OF THE DRAWINGS

The invention, as well as its many advantages, may be further understood by the following detailed description and drawings in which.

DETAILED DESCRIPTION OF THE PREFERRED EMBODIMENT

As stated above, the invention provides a process for fabricating crystalline metal oxide material comprising tin oxide, zirconia, or titania in form as powder, monolith gel or film by first forming a metal oxide material containing —OH surface group through a sol-gel process, and then treating them with $[SiR_m]_nX_zH_y$ compound which reacts with the —OH group to form —$OSiR_m$ surface group, and heating the thus-treated oxide material at a high temperature to crystallize them into a crystalline metal oxide material with high crystallinity, small crystal size (<100 Å) and high surface area (>100 m²/g).

Figure 1:
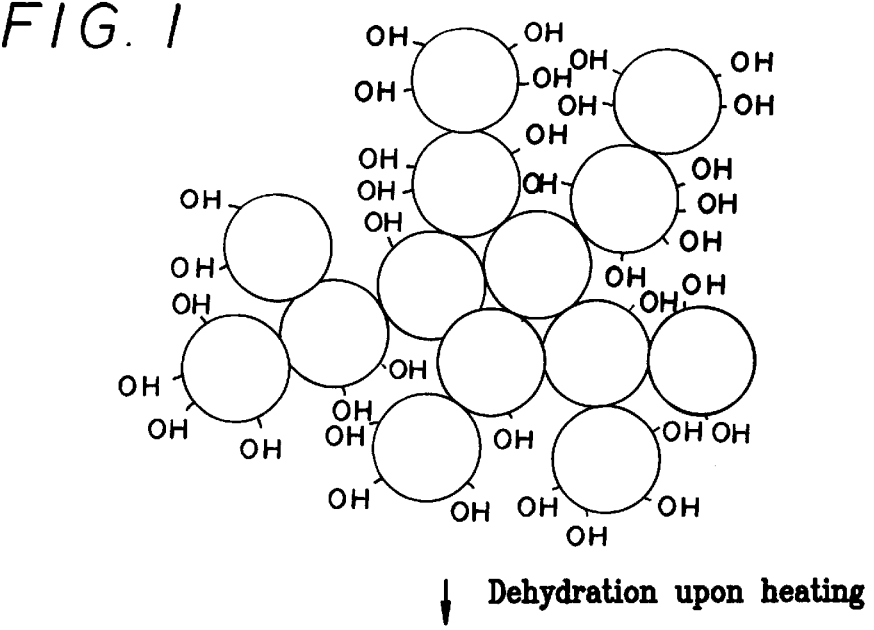
FIG. 1 is a schematic drawing showing the typical microstructural change occurring during heat treatment of the amorphous metal oxide material fabricated by a sol-gel process.
Figure 1:
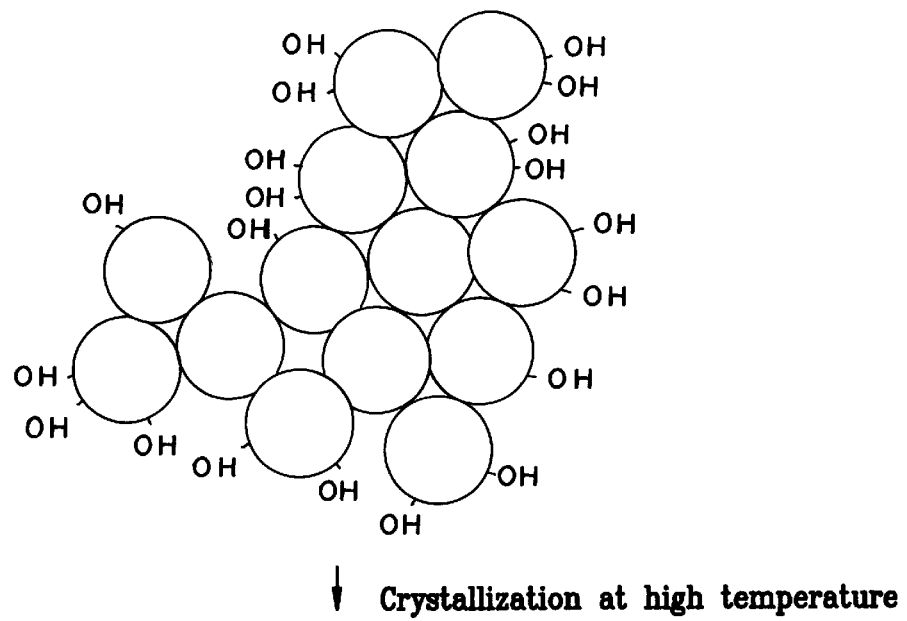
Figure 1:
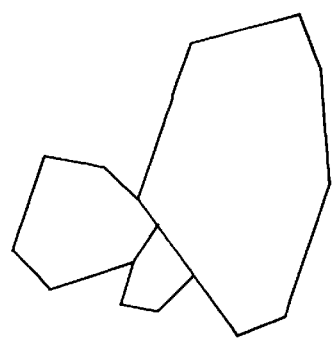
Figure 2:
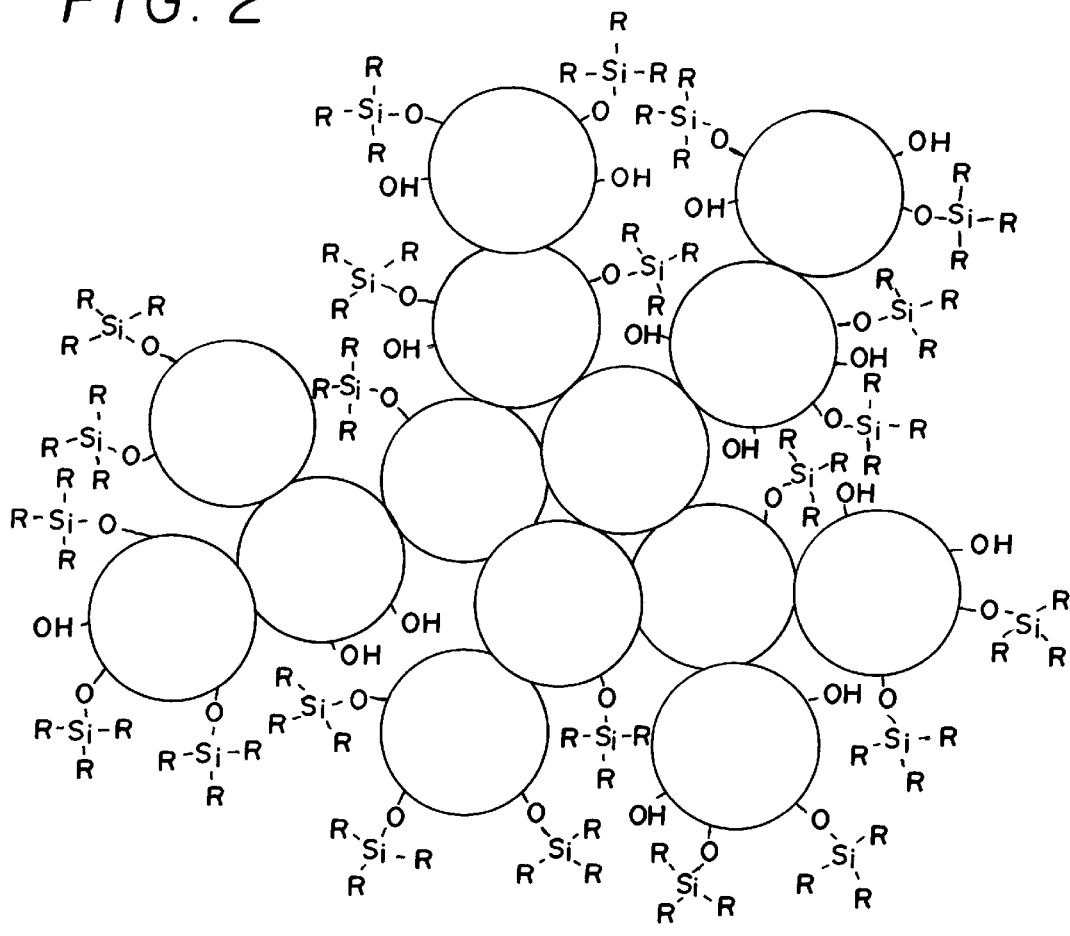
FIG. 2 is a schematic drawing showing the microstructural change occurring during heat treatment of the amorphous material which has been pretreated with a compound having an inactive functional group.
Figure 2:
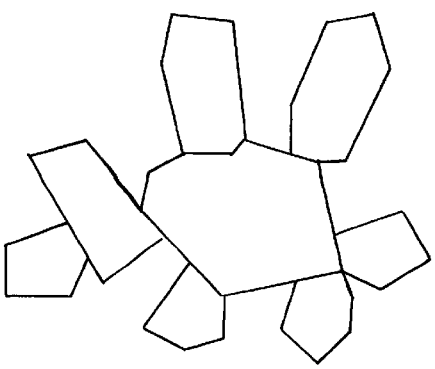

Referring to FIG. 1, a schematic drawing shows the typical microstructural change occurring during heat treatment of the amorphous metal oxide material fabricated by a sol-gel process. In the initial stage of the heat treatment, the constituent particles undergoes dehydration reaction, resulting in reduction in the distance between particles and hence forming agglomerates. At the later stage of the heat treatment, particles undergoes a crystallizaton process in large scale. During this process, the average particle size will increase and pores of small size will disappear, leading to a dramatic reduction in specific surface area. In principle, the process disclosed herein comprises, prior to the heat treating, taking advantage of a reaction between gas molecules and hydroxyl group present on the surface of the particle such that a functional group of low activity is formed instead. Thus, as shown in FIG. 2, particles will not be drawn closer due to reaction of functional groups present on surfaces of different particles in the course of heat treatment. Consequently, each particle crystallizes locally during the heat treatment. Therefore, the growth of crystal can be restricted such that pores of small size and the advantage characteristics of high specific surface area can be retained.

Specifically, the process for fabricating crystalline metal oxide materials with high specific surface area according to the invention comprises steps of:

a. preparing metal oxide material having surface hydroxyl group through a sol-gel process;

b. evaporating compound which has an inactive functional group and will react with the surface hydroxyl group of the oxide to give a functional group the surface low activity adsorbed on the surface of the oxide; and c. heat treating the oxide material for crystallization.

In the process for fabricating crystalline metal oxide materials with high specific surface area, according to the invention, the sol-gel process in step (a) comprises dissolving a metal alkoxide having a general formula of $M(OR')_x$ where M is metal element, R' is a alkyl group, x is a integer of 1~6, or a water soluble metal salt in an aqueous solution, and carrying out hydrolysis and condensation reactions to obtain a sol:

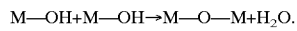

$$M-OH+M-OH \rightarrow M-O-M+H_2O.$$

Then, the gel was washed, dried and calcined to yield metal oxide powder or integrally forming a monolith xerogel. On the other hand, a thin film can be formed first through coating, and then the film is subject to drying and calcination to yield a metal oxide film.

In the process for fabricating crystalline metal oxide materials with high specific surface area, according to the invention, compounds that can form hydrogen ion ($H^+$) or hydroxyl ion ($OH^-$) may be added to change the pH of the solution so as to alter the sol forming rate and the particle dispersion.

In the process for fabricating crystalline metal oxide materials with high specific surface area, according to the invention, metal oxide used in step (a) comprises, for example, tin oxide, zirconium oxide, or titanium oxide with or without containing minor amount (not more than 30 wt %) of one or more other metal elements.

In the process for fabricating crystalline metal oxide materials with high specific surface area according to the invention, the above-mentioned other metal is any metal element selected from the group consisting of platinum, copper, chromium, antimony, yttrium, palladium, gold, aluminum, nickel, cesium, iron, and calcium.

In the process for fabricating crystalline metal oxide materials with high specific surface area according to the invention, the oxide material referred in step (a) comprises sol before drying, or metal oxide powder, xerogel or film dried to various extents.

In the process for fabricating crystalline metal oxide materials with high specific surface area, according to the invention, metal oxide material in step (a) contains an amount of surface hydroxyl group in a range of 0.01 to 50% by weight.

In the process for fabricating crystalline metal oxide materials with high specific surface area, according to the invention, compound having inactive functional group used in step (b) can be represented by a general formula as $[SiR_m]_nX_zH_y$, wherein R's is hydrogen or a same or different alkyl group; when X is nitrogen (N), m=3, n is an integer of 1~3, z=1, and y=3−n; when X is chlorine (Cl), m is an integer of 1~3, n=1, z=4−m, and y=0. Such compound will react with the hydroxyl group on the particle

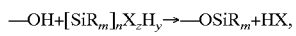

forming $-OSiR_m$ surface group to replace the original hydroxyl group ($-OH$).

In the process for fabricating crystalline metal oxide materials with high specific surface area according to the invention, the above-mentioned alkyl group is anyone selected from methyl, ethyl, or propyl.

In the process for fabricating crystalline metal oxide materials with high specific surface area according to the invention, the drying method stated above may be drying by heating, or supercritical drying.

In the process for fabricating crystalline metal oxide materials with high specific surface area, according to the invention, temperature used for evaporating compound having inactive functional group in step (b) may be in the range of 0~300° C., and preferably, 50~200° C.

In the process for fabricating crystalline metal oxide materials with high specific surface area, according to the invention, temperature used in the crystallization in step (c) may be in the range of 30~2000° C., and preferably, 100~1000° C.

EXAMPLES

The invention will be illustrated in detail with following examples, however, the invention should not be considered to be limited by these examples.

Example 1

6 g of tin tetrachloride pentahydrate ($SnCl_4.5H_2O$) was dissolved in 1000 ml deionized water. A diluted ammonia water (10%) was dropped slowly in this solution under stirring. A sol precipitate was produced. The addition of ammonia water was continued until pH is equal to 2.0. The sol precipitate thus produced was allowed to settle down spontaneously to the bottom of the container. About 700 ml of the supernatant was drawn off. An equal amount of water was added, stirred, and then allowed to stand. This procedure consisting of standing, settling, drawing off supernatant, and adding distilled water was repeated seven times. Thereafter, the sol precipitate was filtered at temperature to remove part of water and then poured in a polyethylene container having a diameter of 4.5 cm. The gel was dried at 34° C. and under 80% relative humidity into a tin dioxide monolith xerogel. One gram of the xerogel (sample A) was placed into a closed container which contained 1 ml of hexamethyldisilazane ($Si(CH_3)_3)_2NH$)(HMDS) and the entire container was heated at 150° C. for 4 hours. Another gram(sample B) did not receive the HMDS treatment. Both samples were then heated in a furnace from room temperature to 500° C. and maintained at this temperature for one hour. Subsequently, these two samples were analyzed by X-ray diffraction, Ultra Violet/Visible/Near-IR Spectroscopy, BET nitrogen adsorption analyses.

Analysis by near-IR spectroscopy revealed that the monolith xerogel as produced contained a hydroxyl group content of 4.65 wt %. The average crystal size thereof was measured on the basis of X-ray diffraction pattern and calculated with the full width at half maximum of (110) diffraction peak using Debye-Scherrer equation:

$$D=0.9\lambda/(\beta_o \cos\theta)$$

D: the average crystal size (Å)

λ: wavelength of X-ray (=1.5418 Å)

$\beta_o$: Full Width at Half Maximum (FWHM)(in radian);

θ: Bragg diffraction angle

Figure 3A:
FIG. 3 is transmission electron micrographs showing microstructures of: (a) the sample A which has been subjected to a HMDS surface treatment prior to heat crystallization; and (b) the sample B which has not been subjected to the HMDS surface treatment.
Figure 3B:
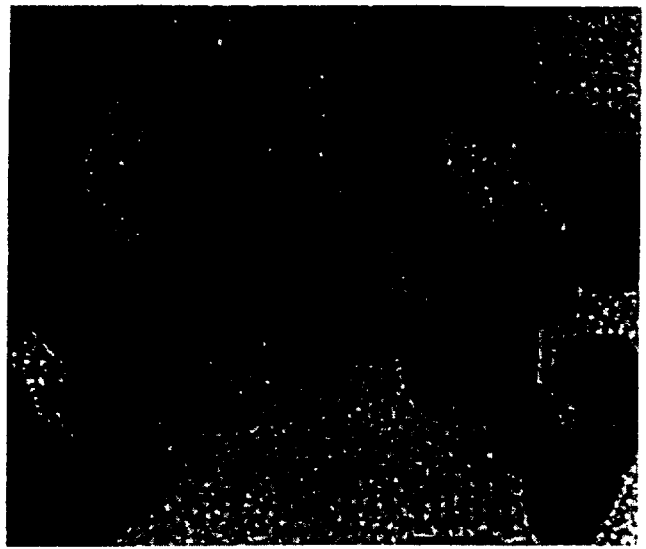

After heat treating, sample A had a crystal size of 22 Å, a specific surface area of 133 m²/g, while sample B had a crystal size of 200 Å and a specific surface area of 40 m²/g. Observation under a transmission electron micrograph revealed clearly the different microstructures between these two samples, as shown in FIG. 3.

Figure 4:
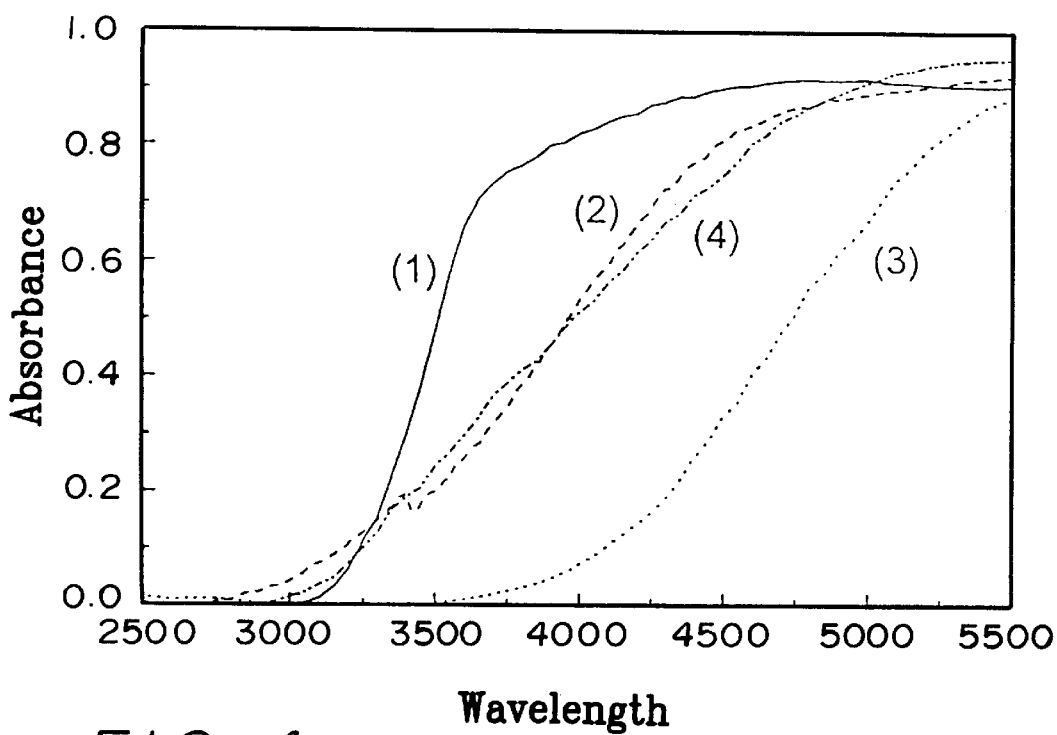
FIG. 4 shows ultraviolet spectra of (1) the reference sample; (2) sample A, 500° C.; (3) sample B, 500° C.; and (4) sample B, 800° C.

Crystallinity of tin dioxide, i.e., extent of defect, may be determined by the position (i.e., wavelength) of the absorption edge in the ultraviolet region appeared in the ultraviolet/visible spectrum. The higher the crystallinity is, the closer the absorption edge energy to the theoretical value (wavelength=3350 Å). FIG. 4 shows the ultraviolet/visible light spectra of various samples in the ultraviolet region. Curve (1) is the spectrum of a reference sample, which is obtained from large grain tin dioxide sample that had been treated at 1000° C. Its absorption started at a wavelength of 3320 Å that is consistent with the theoretical value (3350 Å). Curve (2) and (3) are spectra of sample A and B, respectively. Curve (4) is the spectrum of sample B which had been treated at 800° C. for one hour. By comparing spectra of samples subjected to the same crystallization process (heat treated at 500° C. for one hour), it appears that curve (2) is closer to curve (1) than curve (3), which indicates that sample A has a higher crystallinity, namely, less crystal defect. While a comparison between curves (2) and (4) indicates that sample B should be treated at 800° C. to obtain a crystallinity comparable with that of sample A, whereupon the specific surface area thereof is reduced to about 10 m²/g.

Example 2

A tin oxide sol precipitate was prepared by the same procedure as in Example 1. The opaque sol precipitate formed was allowed to settle down to the bottom of the container. About 700 ml of supernatant was drawn off and an equal amount of water was added, stirred, and then allowed to stand. This procedure consisting of standing, settling, drawing off supernatant, and adding distilled water was repeated seven times. The supernatant aqueous solution was drawn off and 350 ml acetone was added. This procedure was repeated 4 times, whereupon acetone content in the solution is about higher than 99%. Finally, the sol precipitate was placed in an autoclave, and exchanged the acetone therein with a continuous flow of carbon dioxide fluid at a flow rate of about 10 ml/min. for a time period of about 24 hours. Thereafter, the temperature of the autoclave was raised to 40° C. while the pressure therein was maintained at 1400 psi. After 30 minutes, the carbon dioxide was released to obtain tin dioxide powder. One gram of the powder (sample C) was placed in a closed container. 2 ml HMDS was added. The container was heated to 150° C. and kept at this temperature for 5 hours. Another gram of the oxide powder (sample D) was not subjected to HMDS treatment. The two samples were heated at 300° C., 400° C., 500° C., and 600° C., repectively, for one hour.

Figure 5:
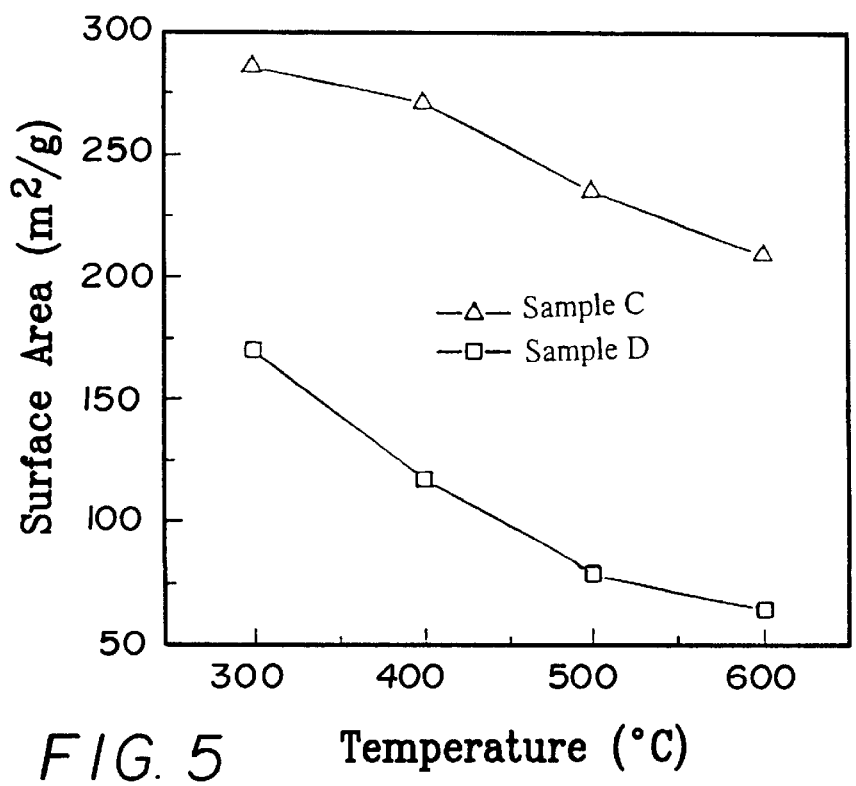
FIG. 5 is a graph showing the effect of crystallization temperature on the specific surface area.

The specific surface areas of the thus-treated samples were measured by BET nitrogen absorption and were shown in FIG. 5. The specific surface area of sample C is kept higher than 200 m$^2$/g. On the other hand, the specific surface area of sample D was only 170 m$^2$/g after being heated at 300° C. for one hour, and was reduced to about 65 m$^2$/g after being heated at 600° C. for one hour.

Example 3

A tin dioxide powder was prepared as in example 2. One gram of the powder was placed in a closed container. 4 ml of trimethylchlorosilane (($CH_3)_3SiCl$) was added. The container was heated to 150° C. and kept at this temperature for 5 hours. After being heat-treated at 150° C. for 1 hours, the specific surface area of this sample was 210 m$^2$/g.

Example 4

70.2 g of tin tetrachloride pentahydrate ($SnCl_4.5H_2O$)was dissolved in 2000 ml deionized water. A diluted ammonia water (10%) was dropped slowly into this solution under vigrous stirring. A sol precipitate was produced. The addition of ammonia water was continued until pH is equal to 2.0. The sol precipitate thus produced was washed with the procedure consisting of standing, settling, drawing off supernatant, and adding distilled water as in example 1 till pH thereof was equal to 4.0 Ammonia water (28%) was then added with stirring till pH thereof was equal to 9.0. After standing for 24 hours, sol particles were dispersed into a transparent sol. 2.9 g antimony trichloride was dissolved in 100 ml methanol. This solution was mixed homogeneously with the tin dioxide solution prepared, where a yellow sol precipitate was formed and pH value here was 2.5. The washing procedure described above was used till pH thereof was 4.0 to remove ammonium and chloride ions. Then, as in Example 2, water in the precipitate was exchanged with acetone which was replaced subsequently with carbon dioxide fluid. After evaporating off the carbon dioxide, a tin dioxide powder doped with antimony was obtained. One gram of the powder (sample E) was placed in a closed container. 10 ml HMDS was added. The container was heated to 150° C. and kept at this temperature for 5 hours. Another gram of the powder (sample F) was not subjected to HMDS treatment. The two samples were heat-treated at 600° C. for one hour. The result of BET nitrogen absorption measurement revealed that, after being subjected to such a heat treatment, the specific surface area of sample E is 200 m$^2$/g and that of sample F was 70 m$^2$/g.

Example 5

Figure 6:
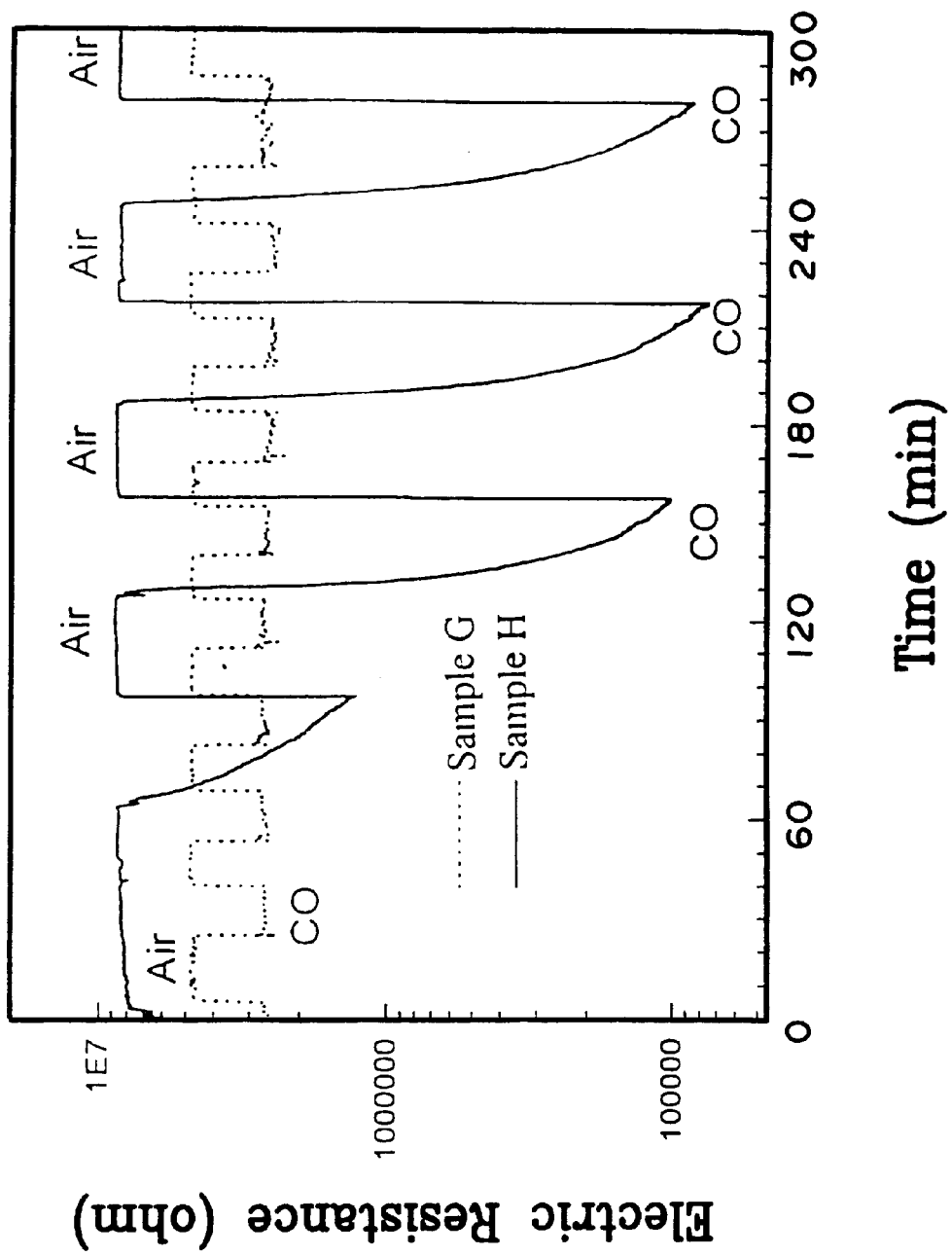
FIG. 6 shows the electric resistance change of a tin dioxide film doped with palladium in an atmosphere of pure air containing 500 ppm of carbon monooxide; sample G: without HMDS treatment; sample H: HMDS-treated.

Gas sensing by tin oxide is based on the variation in conductivity of tin dioxide contained in a gas sensor. Tin dixode with high specific surface area can increase effectively the sensitivity of the gas sensor. A transparent sol was prepared as in example 4. 0.35 g $PdCl_2$ was dissolved in 45 ml ammonia water with pH=10. This solution was mixed homogeneously with the tin dioxide sol prepared above. Films were prepared by spin-coating the solution onto glass substrates, followed by drying at 100° C. for 0.5 hour. A film of sample G was heat-treated directly in 350° C. air for one hour. A film of sample H was placed in a closed container. 10 ml HMDS was added. The container was heated to 150° C., kept at this temperature for one hour and then heat-treated in 350° C. air for one hour. These two samples was used separately to detect 500 ppm carbon monoxide at a temperature of 20° C. detection results were converted into sensitivities according to the following formula:

Sensitivity=Ra/Rc wherein Ra was the electric resistance when pure air was passed; Rc was the electric resistance when air containing carbon monooxide was passed. FIG. 6 shows the detection curves with electric resistance as the ordinate and time as abscissa. It indicates that the sensitivity of sample G was 1.9, whereas the sensitivity of sample H was 109.0 that was 57-fold higher than that of sample G.

Example 6

10 g of zirconyl chloride octahydrate ($ZrOCl_2.8H_2O$) was dissolved in 1000 ml deionized water. A diluted ammonia water (10%) was dropped slowly in this solution under stirring. A sol precipitate was produced. The addition of ammonia water was continued until pH is equal to 9.0. The sol precipitate thus produced was then washed and dried with the procedure as in example 1. A monolith zirconia gel was thus produced. One gram of the gel (sample I) was placed in a reactor contained 2 ml HMDS and then heated at 150° C. for one hour. The another one gram (sample J) did not receive the HMDS treatment. Thereafter, these two samples were subjected simultaneously to heat treatment at 500° C. for one hour. BET nitrogen absorption measurement revealed that, after being subjected to such a heat treatment, the specific surface area of sample I is 135 m$^2$/g and that of sample J was 60 m$^2$/g.

Example 7

6 ml titanium tetrachloride ($TiCl_4$) was dissolved in 500 ml aqeous ethanol solution with a volume ratio of ethanol to deionized water as 4:1. After carrying out a procedure of precipitation, washing and drying as in example 1, a monolith titania gel was obtained. One gram of the gel (sample K) was placed in a reactor contained previously with 3 ml HMDS and then heated at 160° C. for 4 hour. The another one gram (sample L) did not receive the HMDS treatment. Thereafter, these two samples were subjected simultaneously to heat treatment at 500° C. for one hour. BET nitrogen absorption measurement revealed that, after being subjected to such a heat treatment, the specific surface area of sample K is 224 m$^2$/g and that of sample L was 60 m$^2$/g.

Many changes and modifications in the above described embodiments of the invention can, of course, be carried out without departing from the scope thereof. Accordingly, to promote the progress in science and the useful arts, the invention is disclosed and is intended to be limited only by the scope of the appended claims.

What is claimed is:

1. A process for fabricating crystalline metal oxide materials with an average crystalline size of less than 100 Å, comprising:
    (a) forming a metal oxide material containing a surface hydroxyl group through a sol-gel process;
    (b) treating the metal oxide material formed in step (a) with a compound having an inactive functional group where a gaseous molecule of said compound reacts with the hydroxyl group on the surface of said oxide to form a functional group of low activity adsorbed on the surface of the oxide; and
    (c) heat treating the treated metal oxide material of step (b) to allow the oxide material to undergo a crystallization reaction.

2. A process as in claim 1, wherein said sol-gel process in step (a) comprises dissolving a metal alkoxide having a general formula of M(OR')$_x$ where M is metal element R' is an alkyl group, x is an integer of 1 to 6, or a water soluble metal salt in an aqueous solution, and carrying out hydrolysis and condensation reactions to obtain a sol:

$$M\text{—}OH + M\text{—}OH \rightarrow M\text{—}O\text{—}M + H_2O;$$

then, washing, drying and calcining said sol to yield metal oxide powder or monolith xerogel, or, forming a film first through coating, and then drying and calcining said film to yield a metal oxide film.

3. A process as in claim 2, wherein said sol-gel process comprises further addition of compounds that can form hydrogen ion (H$^+$) or hydroxyl ion (OH$^-$) to change the pH of the solution so as to alter the sol forming rate and the particle dispersion.

4. A process as claimed in claim 1, wherein said metal oxide used in step (a) comprises tin oxide, zirconium oxide, or titanium oxide, said oxide containing not more than 30 wt % of one or more other metal elements.

5. A process as in claim 4, wherein said other metal is a element selected from the group consisting of platinum, copper, chromium, antimony, yttrium, palladium, gold, aluminum, nickel, cesium, iron, and calcium.

6. A process as in claim 1, wherein said oxide material in step (a) comprises sol before drying, or metal oxide powder, xerogel or film dried to different extents.

7. A process as in claim 1, wherein said metal oxide material in step (a) contains an amount of surface hydroxyl group in a range of 0.01 to 50% by weight.

8. A process as in claim 2 or 3, wherein said drying comprises drying by heating, or supercritical drying.

9. A process as in claim 1, wherein said temperature for evaporating compound having inactive functional group in step (b) is in the range of 0 to about 300° C.

10. A process as in claim 1, wherein said temperature used in the heating crystallization in step (c) is in the range of 30–2000° C.

11. The process as claimed in claim 9, wherein said temperature is from 50 to about 200° C.

12. The process as claimed in claim 10, wherein said temperature is from 100 to about 1,000° C.

* * * * *